(12) United States Patent
Vega

(10) Patent No.: US 9,216,196 B2
(45) Date of Patent: Dec. 22, 2015

(54) DRINK FOR THE RAPID REPLACEMENT OF CALCIUM IONS IN THE BLOOD STREAM

(75) Inventor: Erlinda Handal Vega, San Salvador (SV)

(73) Assignee: Jose Schafik Colazo Handal, San Salvador (SV)

( * ) Notice: Subject to any disclaimer, the term of this patent is extended or adjusted under 35 U.S.C. 154(b) by 0 days.

(21) Appl. No.: 14/122,821

(22) PCT Filed: Jun. 15, 2011

(86) PCT No.: PCT/SV2011/000001
§ 371 (c)(1),
(2), (4) Date: Jan. 27, 2014

(87) PCT Pub. No.: WO2012/166061
PCT Pub. Date: Dec. 6, 2012

(65) Prior Publication Data
US 2014/0134279 A1    May 15, 2014

(30) Foreign Application Priority Data
May 27, 2011 (SV) .............................. 20110003928

(51) Int. Cl.
*A61K 33/06* (2006.01)
*A23L 1/304* (2006.01)
*A23L 2/52* (2006.01)
*A23L 2/60* (2006.01)

(52) U.S. Cl.
CPC ................. *A61K 33/06* (2013.01); *A23L 1/304* (2013.01); *A23L 2/52* (2013.01); *A23L 2/60* (2013.01); *A23V 2002/00* (2013.01); *A23V 2200/306* (2013.01); *A23V 2250/1578* (2013.01)

(58) Field of Classification Search
None
See application file for complete search history.

(56) References Cited

U.S. PATENT DOCUMENTS

| | | | | |
|---|---|---|---|---|
| 6,036,984 | A * | 3/2000 | Sartorio et al. | 426/72 |
| 6,403,129 | B1 | 6/2002 | Clark et al. | |
| 2005/0100637 | A1 * | 5/2005 | Murray et al. | 426/72 |

OTHER PUBLICATIONS

Bronus, et al. "The Effect of Different Rehydration Drinks on Post-Exercise Electrolyte Excretion in Trained Athletes." Int. J. Sports Med. published in 1998, vol. 19, pp. 56-60.
Carter, et al. "Fluid Replacement During and After Exercise in the Heat." Medicine and Science in Sports and Exercise. Published in 1989, vol. 21, N 5, pp. 532-539.
International Search Report and Written Opinion of the International Search Authority dated Jun. 20, 2013 for International Application No. PCT/SV2011/000001.
Suda, et al. "Modulation of osteoclast differentiation by local factors." Department of Biochemistry, School of Dentistry, Showa University, Tokyo, Japan. Aug. 1995.
Endo "Calcium-Induced Calcium Release in Skeletal Muscle." 2009, Saitama Medical University, Kawagoe, Saitama, Japan.
Li, et al. "Parathyroid hormone stimulates osteoblastic expression of MCP-1 to recruit and increase the fusion of pre/osteoclasts." Department of Physiology and Biophysics, University of Medicine and Dentistry of New Jersey—Robert Wood Johnson Medical School, 675 Hoes Lane, Piscataway, NJ 08854, USA. Nov. 9, 2007;282(45):33098-106. Epub Aug. 9, 2007.
Jilka, et al. "Continuous elevation of PTH increases the number of osteoblasts via both osteoclast-dependent and -independent mechanisms." Division of Endocrinology & Metabolism, Center for Osteoporosis and Metabolic Bone Diseases, Central Arkansas Veterans Healthcare System, University of Arkansas for Medical Sciences, Little Rock, AR 72205, USA. rljilka@uams.edu. Nov. 2010;25(11):2427-37. doi: 10.1002/jbmr.145.
Shu, et al. "The calcium-sensing receptor mediates bone turnover induced by dietary calcium and parathyroid hormone in neonates." Laboratory of Reproductive Medicine, Research Center for Bone and Stem Cells, Nanjing Medical University, Nanjing, Jiangsu, People's Republic of China. May 2011;26(5):1057-71. doi: 10.1002/jbmr.300.
Khosla, et al. "Building bone to reverse osteoporosis and repair fractures." Endocrine Research Unit, College of Medicine, Mayo Clinic, Rochester, Minnesota, USA. Feb. 2008;118(2):421-8. doi: 10.1172/JCI33612.
Suda, et al. "The molecular basis of osteoclast differentiation and activation." Department of Biochemistry, School of Dentistry, Showa University, Tokyo 142-8555, Japan. 2001;232:235-47; discussion 247-50.

* cited by examiner

*Primary Examiner* — Bethany Barham
*Assistant Examiner* — Barbara Frazier
(74) *Attorney, Agent, or Firm* — Eschweiler & Associates, LLC

(57) ABSTRACT

The present invention relates to a beverage that provides rapid uptake of calcium ions into the blood stream in less than ten minutes.

15 Claims, No Drawings

DRINK FOR THE RAPID REPLACEMENT OF CALCIUM IONS IN THE BLOOD STREAM

FIELD OF THE INVENTION

The object of the invention is a beverage containing calcium ions, potassium, carbohydrates such as sugars and electrolytes lost as a result of intense sweating, besides water, flavors and preservatives, having the special feature to provide rapid uptake of calcium ions into the bloodstream.

BACKGROUND OF THE INVENTION

There are countless studies that have been done and done, about the mechanisms that trigger bone resorption processes. It is now clear that the activity of osteoclasts (bone-degrading cells) is mediated by parathyroid gland through parathyroid hormone activate bio chemical signal (1-8).

In the human body exist various chemical forms of calcium: solid as phosphates, carbonates and hydroxyapatite bone tissue constituent materials, fluorapatite in the enamel of the teeth, and ionic state from soluble salts as chloride and calcium acetate.

Calcium in ionic state is extremely important in the human body and performs functions biochemical signal transduction, for example are involved in neuronal synapses, in the system of production of nitric oxide by the vascular endothelium and macrophages, in the mechanism of apoptosis cellular activity of calmodulin as enzyme cofactor, muscle function, etc.

The normal concentration of calcium ions in blood is in the range of 8.1 to 10.4 mg/dL, a decrease of this concentration below 8.0 mg/dL is "perceived" by the parathyroid gland as deficiency of calcium ions and activated immediately biochemical cascade such compensation ion loss "ordering" osteoclasts to take calcium from large reservoir which is the backbone and sent to the bloodstream in the form of ions, thereby restoring the optimum concentration of calcium ions in bloodstream.

A sudden exit of calcium ions from the bloodstream, for example caused by intense sweating, can unbalance the calcium-dependent biochemical cascades and unbalance the operation of the body in general. Replenishing the losses of calcium ions and quickly restore its optimal concentration before Parathyroid gland "receives" the absence of calcium ions and "shoot" the biochemical signal activation of osteoclasts, is vital to prevent bone loss; especially when the ability to form new bone tissue is reduced as in menopause and andropause, which leads to the appearance of osteopenia and osteoporosis.

Currently on the market there are no drink or other calcium compounds from which they can provide rapid uptake of calcium ions into the bloodstream in order to prevent loss of bone mass loss of electrolytes, particularly calcium.

Investigations by our group have resulted optimal composition of salts and compounds which allows rapid absorption of calcium ions and their passage into the bloodstream.

The present invention has its origins in patents, patent application 2006002712 our CNR, but unlike that this is the preparation of a beverage for rapid replacement of calcium ions in the bloodstream which has a simple composition fast acting, in terms of calcium replacement.

DISCLOSURE OF INVENTION

The present invention relates to the preparation of a beverage to counteract sudden calcium ions exit the bloodstream caused by heavy loss of fluids, for example a heavy sweating due to prolonged physical exertion, menopause and andropause processes during episodes called "hot flashes", endocrine disorders, etc.

Drink, object of the present invention contains a mixture of ions which facilitates the absorption of calcium, so that it passes the bloodstream quickly avoiding the signal of the parathyroid gland, which activates osteoclasts to send dissolve bone and calcium ions into the blood stream.

Studies conducted by our research group have shown that women in menopause period (climacteric), during the "hot flashes" and intense sweating after they lose up to 3.5 mg of calcium in each sweating, and that athletes sweat lost between 3.5 and 7.5 mg of Ca per dL of sweat.

Rapid and intense output calcium several times daily causes calcium deficiency that affect the functioning of many important biochemical mechanisms of the immune system, blood pressure and neuronal signal transmission, among others. Abrupt exit soluble calcium is rapidly compensated by the calcium pumps then replenished calcium, to bring it to its normal concentration in the calcium-dependent different systems of the organism, through a complex mechanism of dissolution of bone tissue mediated process exacerbated by activity of osteoclasts commanded by the parathyroid gland, which contributes significantly to the loss of hydroxyapatite by bone producing osteopenia and osteoporosis later.

This dissolution process affects bone tissue and cancellous bone tissue which has a larger contact surface and therefore has a greater surface for osteoclast activity. In this category of bone and vertebrae are the ends of long bones such as the femur and humerus.

The present invention comprises a mixture of calcium salts, carbohydrates sweeteners and ions to facilitate rapid absorption of calcium and its incorporation into the bloodstream, helping to restore the blood calcium ion concentration.

Composition Example 1

Were prepared 3 servings of 500 mL, with composition:
0.513 g of soluble calcium compound, extract lemon/lime, 1.0 g glucose, 0.1 g of potassium sorbate, 4 g of sucrose, 0.01 g sodium chloride.

Value of $[Ca]^{2+}$ in sweat:

| patient | |
|---|---|
| X | 3.9 mg/dL |
| Y | 7.2 mg/dL |

Measurements of [Ca] 2+ before and after taking prepared Ca

| Patient | $[Ca]^{2+}$ mg/dL blood before taking | $[Ca]^{2+}$ mg/dL of blood 10 minutes to take |
|---|---|---|
| X | 9.3 | 9.9 |
| Y | 8.9 | 9.0 |
| Z | 8.1 | 8.4 |

(Normal range [Ca] 2+ in blood Ca 8.1 to 10.4 mg/dL)

Composition Example 2

0.514 g of soluble calcium compound, 500 mL of water, extract tangerine, 0.5 g glucose, 0.1 g of potassium sorbate, 4 g of sucrose, 0.01 g sodium chloride.

Measurements of [Ca] 2+ before and after taking prepared Ca

| Patient | $[Ca]^{2+}$ mg/dL blood before taking | $[Ca]^{2+}$ mg/dL of blood 10 minutes to take |
|---------|---------------------------------------|------------------------------------------------|
| Z       | 8.4 mg/dL                             | 9.0 mg/dL                                      |

The invention claimed is:

1. A beverage, comprising:
a concentration of 0.513 g of calcium ions, 0.1 g of potassium sorbate, 0.01 g of sodium chloride, and between 4.5 and 5.0 g of carbohydrate sweetener per 500 mL of water, wherein the beverage elevates a blood concentration of calcium ions within 10 minutes or less of consumption.

2. The beverage of claim 1, wherein the carbohydrate sweetener comprises glucose.

3. The beverage of claim 2, wherein the concentration of glucose comprises 1.0 g per 500 mL of water.

4. The beverage of claim 1, wherein the carbohydrate sweetener comprises sucrose.

5. The beverage of claim 4, wherein the concentration of sucrose comprises 4 g per 500 mL of water.

6. A beverage, comprising:
a concentration of 0.514 g of calcium ions, 0.1 g of potassium sorbate, 0.01 g of sodium chloride, and between 4.5 and 5.0 g of carbohydrate sweetener per 500 mL of water, wherein the beverage elevates of a blood concentration of calcium ions within 10 minutes or less of consumption.

7. The beverage of claim 6, wherein the carbohydrate sweetener comprises glucose.

8. The beverage of claim 7, wherein the concentration of glucose comprises 0.5 g per 500 mL of water.

9. The beverage of claim 6, herein the carbohydrate sweetener comprises sucrose.

10. The beverage of claim 9, wherein the concentration of sucrose comprises 4 g per 500 mL of water.

11. A beverage, comprising:
a concentration of between 0.513 and 0.514 g of calcium ions, 0.1 g of potassium sorbate, 0.01 g of sodium chloride, and between 4.5 and 5.0 g of carbohydrate sweetener per 500 mL of water, wherein the beverage prevents activation of osteoclasts by a parathyroid gland by elevating a blood concentration of calcium ions within 10 or less minutes of consumption.

12. The beverage of claim 11, wherein the carbohydrate sweetener comprises glucose.

13. The beverage of claim 12, wherein the concentration of glucose is between 0.5 and 1.0 g per 500 mL of water.

14. The beverage of claim 11, wherein the carbohydrate sweetener comprises sucrose.

15. The beverage of claim 14, wherein the concentration of sucrose comprises 4 g per 500 mL of water.

\* \* \* \* \*

UNITED STATES PATENT AND TRADEMARK OFFICE
CERTIFICATE OF CORRECTION

| | | |
|---|---|---|
| PATENT NO. | : 9,216,196 B2 | |
| APPLICATION NO. | : 14/122821 | |
| DATED | : December 22, 2015 | |
| INVENTOR(S) | : Erlinda Handal Vega | |

It is certified that error appears in the above-identified patent and that said Letters Patent is hereby corrected as shown below:

In the Claims

Column 4, Claim 9, Line 8 Please replace "…claim 6, herein the…." with --…claim 6, wherein the…--

Signed and Sealed this
Eighth Day of March, 2016

Michelle K. Lee
*Director of the United States Patent and Trademark Office*